US00PP09218P

United States Patent [19]

Trees

[11] Patent Number: Plant 9,218

[45] Date of Patent: Jul. 25, 1995

[54] GERANIUM PLANT NAMED PINK HEART

[75] Inventor: Scott C. Trees, Arroyo Grande, Calif.

[73] Assignee: Geo. J. Ball, Inc., West Chicago, Ill.

[21] Appl. No.: 341,910

[22] Filed: Nov. 15, 1994

[51] Int. Cl.[6] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Burns, Doane, Swecker & Mathis

[57] ABSTRACT

A new and distinct *Pelargonium*×*hortorum* cultivar named Pink Heart is provided. This new Zonal Geranium cultivar was the result of a controlled breeding program wherein a plant designated 9380E (non-patented in the United States) was pollinated by the Rio cultivar (non-patented in the United States). The new cultivar forms attractive medium pink florets with a distinct dark rose freckle on each petal. Attractive dark green foliage is well retained during shipment. The growth habit is self-branching and does not require the use of a growth regulator.

1 Drawing Sheet

SUMMARY OF THE INVENTION

The present invention comprises a new and distinct Geranium cultivar, botanically known as *Pelargonium*-×*hortorum* Bailey, and hereinafter is referred to by the cultivar name Pink Heart.

The new cultivar is a product of a planned breeding program which had the objective of the creation of a new Geranium cultivar that exhibits uniform flowers, dark green foliage, a medium self-branching growth habit that requires no growth regulator, a propensity for rapid rooting, and a stable foliage coloration during shipment.

The breeding program that resulted in the production of the new cultivar of the present invention was carried out in a controlled environment during 1990 at Arroyo Grande, Calif., U.S.A. The female parent (i.e., seed parent) was a plant designated 9380E (non-patented in the United States) which exhibits single pink florets having a dark rose freckle on each petal and medium-to-light foliage. The male parent (i.e., pollen parent) was the Rio cultivar (non-patented in the United States) which exhibits single pink florets with dark red freckles on the petals and forms dark green foliage. The parentage of Pink Heart can be summarized as follows:

9380E×Rio.

Pink Heart was discovered and selected during 1991 as a highly distinctive flowering plant from among the pogeny of the stated cross at Arroyo Grande, Calif., U.S.A. This plant was initially designated BFP-537.

It was found that the new cultivar of the present invention:

(a) exhibits attractive single medium pink florets with a distinct dark rose freckle on each petal and with the upper two petals commonly having slightly larger areas of dark rose than the lower three petals,
(b) forms attractive dark green foliage, and
(c) exhibits a medium self-branching growth habit.

When plant material of the Pink Heart cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the Pink Heart cultivar was accomplished when vegetative cuttings was taken from the initial selection in a controlled environment at Arroyo Grande, Calif., U.S.A., by a technician working under the direction and supervision of the originator of the new cultivar. Horticultural examination of plants resulting from such asexual propagation during 1991 has demonstrated that the combination of characteristics as herein described for the Pink Heart cultivar is firmly fixed and is retained through successive generations of such reproduction.

The new Pink Heart cultivar has not been observed under all possible environmental conditions. Accordingly, the described phenotype may vary somewhat with variations in the environment, such as temperature, light intensity, and day length.

Of the many commercial cultivars, the Rio cultivar (non-patented in the United States) is considered to be the most similar to the new Pink Heart cultivar. When the new cultivar of the present invention is compared to the Rio cultivar, it is found that the Pink Heart cultivar has considerably more florets per umbel (e.g., approximately 33 to 40 vs. approximately 15 to 22). Additionally, the florets of the Pink Heart cultivar are darker in coloration and have larger, overlapping petals as specified in greater detail hereafter.

The new cultivar of the present invention is being marketed by Geo. J. Ball, Inc. under the Showcase trademark.

BRIEF DESCRIPTION OF THE PHOTOGRAPHS

The accompanying photographs show typical characteristics of the new Pink Heart cultivar with colors generally being as nearly true as it is reasonably possible to make the same in color illustrations of this character. The plants were being grown in greenhouses at West Chicago, Ill., U.S.A.

DETAILED DESCRIPTION

Figure 1:
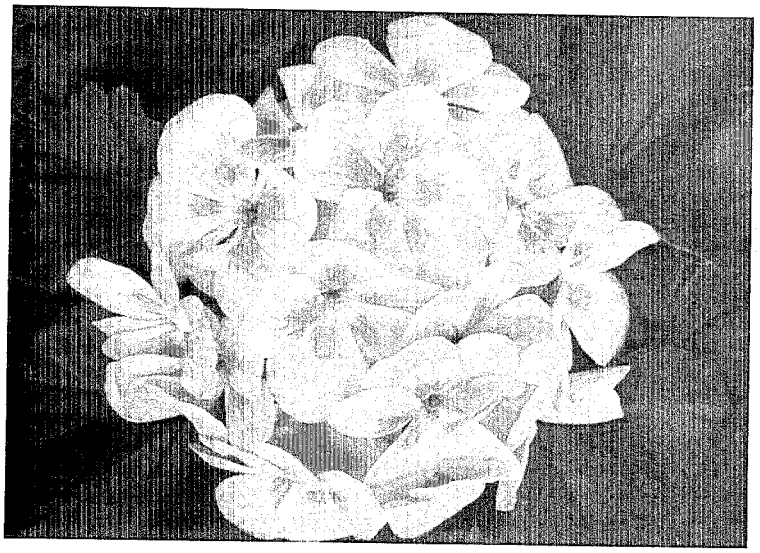
FIG. 1 illustrates the general appearance of a fully-opened umbel as seen from above together with the contrasting dark green foliage.
Figure 2:
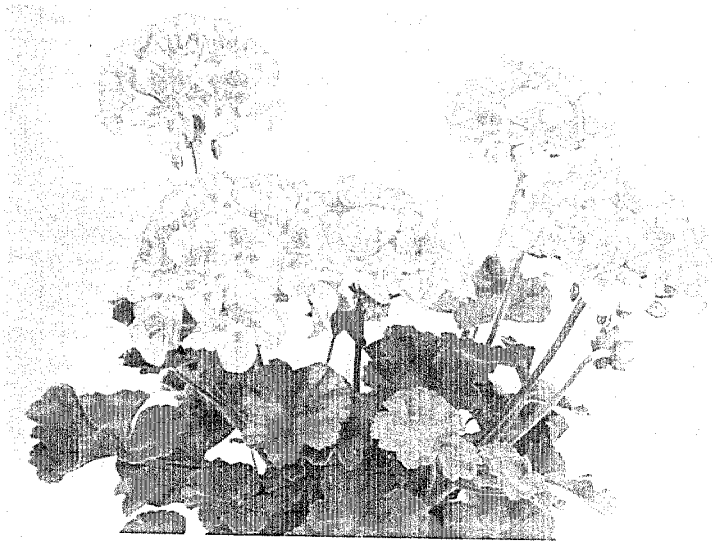
FIG. 2 illustrates the general appearance of the upper portion of an overall plant as seen from the side wherein a plurality of umbels are presented. The dark green foliage coloration is believed to be more accurately depicted in FIG. 1 than in FIG. 2.

The following observations, measurements and comparisons describe plants grown in Ball FloraPlant's greenhouses at West Chicago, Ill., U.S.A. under greenhouse conditions which approximate those generally used in commercial practice. In the following description, color references are made to the R.H.S. Colour Chart of The Royal Horticultural Society, London, England. The color values were determined between 9:00 and 10:00 a.m. on Jul. 21, 1994, under natural light conditions of 2,000 footcandles.

Classification:

*Botanical.*—*Pelargonium*×*hortorum* Bailey, cv. Pink Heart.

*Commercial.*—Zonal Geranium.

INFLORESCENCE

A. Umbel:

*Average diameter.*—Approximately 9.5 to 11.0 cm. compared to approximately 9.5 to 10.0 cm. for the Rio cultivar.

*Average depth.*—Approximately 5.0 to 6.0 cm. compared to approximately 5.5 to 6.0 cm. for the Rio cultivar.

*Peduncle length.*—Approximately 11.0 to 15.0 cm. compared to approximately 11.0 to 12.0 cm. for the Rio cultivar.

*Pedicel length.*—Approximately 3.2 to 3.4 cm. compared to approximately 2.5 to 3.5 cm. for the Rio cultivar.

*Number of umbels/plant.*—When grown in a 10 cm. pot at 9 weeks after the sticking of a rooted cutting, there commonly are 5 to 8 umbels per plant. This compares to approximately 6 to 9 umbels per plant for the Rio cultivar.

*Number of florets/umbel.*—When grown in a 10 cm. pot at 9 weeks after the sticking of a rooted cutting, there commonly are approximately 33 to 40 florets per umbel. This compares to approximately 15 to 22 florets per umbel for the Rio cultivar.

B. Corolla:

*Average diameter.*—Approximately 4.5 to 4.6 cm. compared to approximately 3.9 to 4.1 cm. for the Rio cultivar.

*Form.*—Both the Pink Heart cultivar and the Rio cultivar are single. However, the petals of the Pink Heart cultivar commonly are larger than those of Rio cultivar (e.g., approximately 1.8 to 2.0 cm. compared to approximately 1.4 to 1.5 cm).

*Number of petaloids.*—Neither the Pink Heart cultivar nor the Rio cultivar forms petaloids.

*Color.*—General tonality from a distance of three meters: pink with dark eye. Adaxial: Red-Purple Group 73B with a patch of Red Group 52A on each petal (with larger areas of 52A on the two upper petals). This compares to Red-Purple Group 62B with patch of Red-Purple Group 57A on each petal (with larger areas of 57A on the upper two petals) for the Rio cultivar. Abaxial: Red-Purple Group 73C with veins of Red-Purple Group 73B. This compares to Red-Purple Group 62C for the Rio cultivar.

C. Bud:

*Shape.*—Oval-pointed.

*Color.*—Adaxial: Red-Purple Group 73B compared to Red-Purple Group 62B for the Rio cultivar. Abaxial: Red-Purple Group 73C compared to Red-Purple Group 62C for the Rio cultivar.

D. Reproductive organs:

*Androecium.*—The anthers are commonly approximately 2 mm. in length. The pollen color for both the Pink Heart cultivar and the Rio cultivar is Orange-Red Group 31A. The filaments commonly are approximately 4 to 7 mm. in length.

*Gynoecium.*—The pistil length commonly is approximately 11 mm. There is a single stigma which commonly has a length of approximately 7 mm. which commonly branches into 5 parts, and, the style length commonly is approximately 4 mm.

*Fertility.*—Usually does not produce fruits in the absence of mechanical fertilization.

E. Spring flowering response period: Approximately 6 to 7 weeks from rooted cuttings under greenhouse conditions.

F. Outdoor flower production: Freely flowering under outdoor growing conditions with substantially continuous blooming. The petal coloration commonly does not fade as does that of the Rio cultivar. Also, the plants are more vigorous than those of the Rio cultivar.

G. Durability: Ships well.

PLANT

A. Foliage: Dark green with no pronounced zone.

*Form.*—Reniform, with cordate base.

*Margin.*—Crenate.

*Color.*—Adaxial: Yellow-Green Group 147A for both the Pink Heart cultivar and the Rio cultivar. Abaxial: Yellow-Green Group 146A for both the Pink Heart cultivar and the Rio cultivar.

*Size.*—Approximately 7.5 to 8.0 cm. at the widest point and approximately 6.0 to 6.7 cm. at the narrowest point. This compares to approximately 6.9 to 7.2 cm. at the widest point and approximately 6.0 to 6.2 cm. at the narrowest point for the Rio cultivar. A medium self-branching growth habit is exhibited in the absence of the use of a growth regulator.

*Tolerance to botrytis.*—None claimed. However, the single flower form tends to reduce a problem from Botrytis.

B. General appearance and form:

*Internode length.*—Commonly varies from approximately 1.5 to 2.0 cm.

*Branching pattern.*—Freely basal branching. No pinching is required to obtain self-branching. A medium self-branching growth habit is exhibited in the absence of the use of a growth regulator.

*Height.*—Approximately 23 26 cm. above a 10 cm. pot at 9 weeks under standard greenhouse conditions.

I claim:

1. A new and distinct Geranium cultivar named Pink Heart, substantially as herein shown and described, which:

(a) exhibits attractive single medium pink florets with a distinct dark rose freckle on each petal and with the upper two petals commonly having slightly larger areas of dark rose than the lower three petals, (b) forms attractive dark green foliage, and (c) exhibits a medium self-branching growth habit.

* * * * *